United States Patent [19]

Chou et al.

[11] 4,285,972

[45] Aug. 25, 1981

[54] METHOD OF TREATING SCOURS

[75] Inventors: Billy J. Chou, Paoli; John Yelnosky, Warrington; Richard L. Riley, North Wales, all of Pa.

[73] Assignee: William H. Rorer, Inc., Fort Washington, Pa.

[21] Appl. No.: 65,982

[22] Filed: Aug. 13, 1979

[51] Int. Cl.$^3$ .................... A61K 31/17; A61K 31/155
[52] U.S. Cl. .................... 424/326; 424/246; 424/250; 424/251; 424/263; 424/267; 424/270; 424/272; 424/273 P; 424/273 R; 424/275; 424/278
[58] Field of Search ............... 424/326, 246, 250, 251, 424/263, 267, 270, 272, 273 P, 273 R, 275, 278; 260/553 A

[56] References Cited

PUBLICATIONS

Arzneimittel Forschung (Drug Research), vol. 28, No. 11, pp. 1433 to 1480, Aug. 1978.
Cunha et al., Chem. Abst., vol. 41, cols. 6941–6942 (1947).
Chin et al. I, vol. 54, col. 18790 (1960).
Skowrouska–Serafin et al., Chem. Abstracts, vol. 55, cols. 3450–3451 (1961).
Bogdan et al., Chem. Abstracts, vol. 55, col. 5663 (1961).
Chin et al. II, vol. 55, col. 10712 (1961).
Jungstand et al., Chem. Abstracts, vol. 62, cols. 8286–8227 (1965).
Jakimowska et al., Chem. Abstracts, vol. 63, col. 1094 (1965).
Wutkiewicz et al., Chem. Abstracts, vol. 64, col. 20441 (1966).
Urbanski et al., Chem. Abstracts, vol. 64, abst. of col. 1241 (1966).

*Primary Examiner*—John D. Randolph
*Attorney, Agent, or Firm*—Ernest G. Szoke; James A. Nicholson

[57] ABSTRACT

Scours in animals, particularly new-born calves, lambs, piglets and foals are treated with a compound containing an effective amount of an antidiarrheal amidinourea.

26 Claims, No Drawings

METHOD OF TREATING SCOURS

BACKGROUND

Scours, particularly in new-born calves, lambs, piglets, and foals, is a major cause of death, especially under intensified commercial animal husbandry practices where the disease accounts for large economic losses. The disease occurs commonly in calves, pigs, lambs and foals under 10 days of age and is characterized by varying degrees of diarrhea and dehydration.

The disease known as adult bovine scours is also prevalent among wintering adult cattle, frequently leading to death losses. The etiology and pathology of the disease are not well understood, but the disease is generally attributed to factors which cause ordinarily harmless intestinal bacteria to proliferate. Regardless of the cause, the result is a net loss of electrolytes and fluids into the intestinal lumen. The loss of electrolytes and fluids results in acidosis and dehydration leading to other acute toxic effects. Generally, treatment for this condition involves correction of the acid base imbalance and rehydration and treatment of intestinal infections, if present. Such treatments may include administration of antibacterial agents and electrolyte solutions orally. The usual antibacterial agents are antibiotics and sulfonamides.

In recent years, a variety of amidinoureas have been shown to be effective antidiarrheal agents in laboratory test animals and in humans. Pharmaceutically effective antidiarrheal agents such as the amidinoureas are not known for use in the treatment of scours, particularly in calves, lambs and piglets, where annual losses to this disease are high. These compounds have demonstrated their activity in laboratory animals under test conditions designed to mimic gastrointestinal disorders in humans by inducing symptomatic diarrhea in the test animals. Such amidinoureas and their pharmaceutical activity are described in *Arzneimittel Forschung, Drug Research* 28 (II), 1433–1480, (1978). It has now been found that these amidinoureas are particularly effective in reducing morbidity and mortality rate in calves, lambs, piglets and foals suffering from scours, and in adult cattle suffering from bovine winter scours, when orally administered to such animals in effective amounts.

SUMMARY OF THE INVENTION

This invention pertains to novel veterinary compositions containing an effective amount of an antidiarrheal amidinourea and for the use of such compositions in the treatment of animal scours, particularly for the treatment of calves, lambs, piglets, foals, and cattle, and more particularly, for the treatment of new-born calves, piglets and lambs for the prevention and treatment of scours thereby reducing the mortality rate especially for new-born calves, lambs, piglets and foals afflicted with scours. The effective amidinourea is administered in the form of veterinary compositions formulated as tablets, capsules or liquids suitable for oral administration or the amidinourea may be formulated as a dietary supplement suitable for incorporating into the solid or liquid dietary intake of the afflicted animals. The amidinourea can, if desired, be combined with other therapeutic agents or with other suitable excipients.

Losses from calf scours are perhaps the single most serious economic loss of any disease or condition in cattle. It affects about 10% of the 50,000,000 calves born in the United States each year.

The causes of calf scours are varied and not completely understood. Infectious agents include *E. coli*, salmonella, IBR virus (infectious bovine rhinotracheitis) and "Nebraska virus". Ancillary causes such as failure of the calf to obtain sufficient colustrum, stress, contaminated environment and physiologic immaturity all contribute to the problem.

The economic loss due to baby pig scours is nearly as great. Generally caused by *E. coli*, it is the largest source of mortality in the swine industry.

*E. coli* is generally the cause of outbreaks of neoatal diarrhea in lambs. While the economic losses do not approach either of the above, it is still significant to the industry. Young food-producing animals are not the only ones affected by diarrhea BVD (bovine virus diarrhea), caused by a myxovirus and bovine winter dysentary, caused by vibrio jejuni are important factors in the cattle industry. Neither disease condition can be treated very effectively with drugs presently available, though there are many antidiarrheal agents on the market which are used in the treatment of animal scours. Electrolyte solutions, antibiotics, sulfonamides and nitrofurans make up the great majority. Many contain various binding, coating, absorbing and adsorbing agents and astringents. A few have scopolamine, the only common drug being used to slow peristalsis. It is, therefore, an object of this invention to provide an effective treatment for animal scours, particularly in new-born calves, lambs and piglets, i.e. less than ten days old.

It is a further object of this invention to reduce the mortality and morbidity rate of calves, lambs, piglets and foals by including an effective antiscouring amidinourea in the diet of new-born calves, lambs, piglets and foals.

It is still a further object of this invention to provide an effective composition for the prevention and treatment of scours in animals comprising an antiscouring amidinourea in a suitable dosage form or as a feed supplement in combination with suitable excipients and adjuvants of the type noted above.

DETAILED DESCRIPTION OF THE INVENTION

Food-producing animals can suffer from scours, usually during the first ten days of life (neonatal diarrhea). It is a particular problem of serious economic concern in cattle, swine and sheep and methods for control of the disease in these species is especially important.

The amidinoureas which are suitable for use in the method of this invention and which comprise the principal active ingredient in the veterinary compositions of this invention are the compounds of the formula:

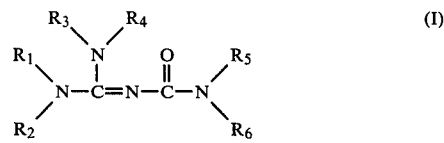

wherein one of $R_1$ or $R_5$ is phenyl, phenyl in which one or more of the hydrogens is substituted by halo, lower alkyl, halo lower alkyl, nitro, lower alkoxy, hydroxy, aryl lower alkoxy, acyloxy, cyano, halo lower alkoxy, or lower alkyl sulfonyl; aralkyl, pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and the other of $R_1$ and $R_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when $R_1$ is phenyl, phenyl substituted as above, aralkyl, pyridyl or pyridyl substituted as above $R_5$ together with $R_6$ and the nitrogen to which $R_5$ and $R_6$ are attached may form a 5 or 6 membered heterocyclic ring which may include 0 to 2 additional hetero atoms which may be either oxygen, nitrogen or sulfur; and when $R_5$ is phenyl, phenyl substituted as above, aralkyl, pyridyl, or pyridyl substituted as above, $R_1$ and $R_2$ together with the nitrogen to which they are attached may be a 5 or 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl; and their pharmaceutically acceptable acid addition salts.

As employed above and throughout the disclosure, the following terms, unless otherwise indicated, shall be understood to have the following meanings:

"alkyl" means a saturated aliphatic hydrocarbon which may be either straight or branched chain, lower alkyl being preferred; also included are the cycloalkyl groups such as cyclohexyl, cyclopropyl, etc. and the cycloalkyl lower alkyl groups such as cyclopropylmethyl and the like.

"lower alkyl" means an alkyl group as above, having 1 to 6 carbon atoms. Suitable lower alkyl groups are methyl, ethyl, propyl, isopropyl, butyl, sec-butyl, tert-butyl, pentyl and isopentyl.

"cycloalkyl" means an aliphatic monocyclic saturated carbocyclic group having 3 to 6 carbon atoms, preferably cyclopropyl, cyclopentyl and cyclohexyl.

"alkenyl" means an unsaturated aliphatic hydrocarbon which contains one or more double bonds and which may be straight or branched chain with lower alkenyl, i.e., alkenyl of 2 to 6 carbons being preferred.

"lower alkenyl" means alkenyl of 2 to 6 carbon atoms such as ethylene, propylene, butylene, isobutylene, etc.

"alkynyl" means an unsaturated aliphatic hydrocarbon containing one or more triple bonds with lower alkynyl, i.e. alkynyl of 2 to 6 carbons being preferred.

"lower alkynyl" means alkynyl of 2 to 6 carbon atoms such as propargyl, butynyl, pentynyl, etc.

"aryl" means phenyl and substituted phenyl.

"substituted phenyl" means a phenyl group in which one or more of the hydrogens has been replaced by the same or different substituents including halo, lower alkyl, halo lower alkyl, nitro, amino, acylamino, hydroxy, lower alkoxy, aryl-lower alkoxy, acyloxy, cyano, halo-lower alkoxy or lower alkyl sulfonyl.

"aralkyl" means an alkyl (preferably a lower alkyl) in which one or more hydrogens is substituted by an aryl moiety (preferably phenyl or substituted phenyl), e.g. benzyl, phenethyl, etc.

"5 and 6 membered heterocyclic group" means a 5 or 6 membered ring having 1 to 3 hetero atoms which may be nitrogen, oxygen or sulfur including pyridyl, 2-pyridyl or 3-pyridyl; pyrimidyl, pyrazolyl, imidazolyl, furyl, thienyl, oxazolyl, thiazolyl, piperidyl, piperazenyl, morpholinyl, thiomorpholinyl, etc. with the pyridyl groups being preferred.

"substituted pyridyl" means a pyridyl in which one or more of the hydrogens on the ring carbons have been replaced by substituents as given above with respect to substituted phenyl. The pyridyl substituents may be either 2-, 3-, or 4-pyridyls; preferred substituted pyridyls are those having substituents on the carbon or carbon atoms vicinal to the carbon attached to the amidino or urea nitrogen.

The terms "halo" and "halogen" include all four halogens; namely, fluorine, chlorine, bromine and iodine.

Halo alkyl and halophenyl include alkyl or phenyl groups having more than one halo substituent which may be the same or different such as trifluoremethyl, 1-chloro-2-bromo ethyl, chlorophenyl, 2-chloro-6-bromophenyl, etc.

The term "acyl" means an organic acid radical, preferably a lower alkanoyl or aroyl, e.g. acetyl, propionyl, benzoyl, benzenesulfonyl, etc.

The term "acyloxy" is intended to mean an organic acid radical such as acetoxy, propionoxy, benzoyloxy, and the like.

The term "acylamino" is intended to mean an organic amido group of the RCONH type where R is an organic radical preferably lower alkyl or aryl lower alkyl.

The term "lower alkanoyl" is intended to include the acid radical of a lower alkanoic acid such as acetyl, propionyl and the like.

It should be understood that whereas the structure of the starting materials are shown here in a particular configuration for purposes of illustration, the compounds may exist in various enolized or tautomeric forms, particularly where one of $R_3$ and $R_4$ is hydrogen, shown for example, by the following formula:

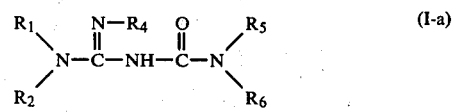

Certain of the compounds can also be obtained as hydrates or in different polymorphic forms. The structures used herein to designate novel compounds are intended to include the compound shown along with its alternative or transient states.

Among the amidinoureas of Formula I, a particularly preferred group of amidinoureas suitable for use in the composition and method of this invention are those in which the $R_5$ substituent is a phenyl or substituted phenyl and particularly a phenyl having substituents in the 2 and 6 positions (i.e. ortho to the carbon attached to the urea nitrogen). Such preferred compounds can be represented by the formula:

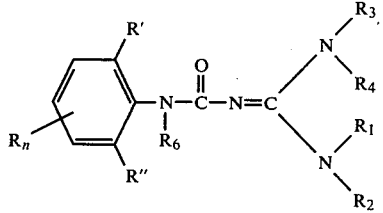

wherein $R_1$, $R_2$, $R_3$, $R_4$ and $R_6$ all have the same meanings as above, and $R_n$ represents one, two or three substituents in any one or more of the para and meta positions which substituents may be hydrogen, halo, lower alkyl, halo lower alkyl, nitro, lower alkoxy, hydroxy, aryl lower alkoxy, acyloxy, halo lower alkoxy, or lower alkyl sulfonyl; R' and R" are hydrogen, halo, lower alkyl, halo lower alkyl, nitro, lower alkoxy, hydroxy, aryl lower alkoxy, acyloxy, halo lower alkoxy, or lower alkyl sulfonyl; and $R_n$ represents one, two or three substituents in any one or more of the para and meta positions which substituents may be hydrogen, halo, lower alkyl, halo lower alkyl, nitro, lower alkoxy, hydroxy, aryl lower alkoxy, acyloxy, halo lower alkoxy, or lower alkyl sulfonyl.

Particularly preferred compounds of Formula I-a are those wherein the phenyl substituents are lower alkyl, lower alkoxy, or halo; and one of $R_1$, $R_2$, $R_3$ and $R_4$ is hydrogen, and the others are lower alkyl, halo lower alkyl, or lower alkoxy lower alkyl. The preferred lower alkyl substituents are methyl, ethyl, propyl, and isopropyl. The preferred halo substituents are chlorine and bromine. The preferred halo lower alkyl substituents are chloromethyl and trifluoromethyl.

A most preferred group of amidinoureas suitable for use in the practice of this invention are the compounds of the formula:

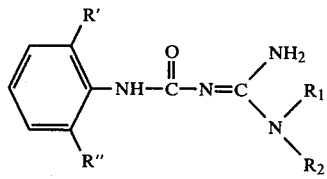

wherein $R_1$ and $R_2$ are each hydrogen, lower alkyl, lower alkoxy or hydroxy; and R' and R" are each hydrogen, halo, or lower alkyl.

The compounds of Formula I, I-a, II or III can be used in the practice of this invention in the form of the base or as salts prepared by reacting the compounds of Formula I with pharmaceutically acceptable acids. Suitable acid addition salts are for example, the salts derived from the following organic and inorganic acids: hydrochloric acid, nitric acid, sulfuric acid, phosphorous acid, ortho-phosphoric acid, etc.; aliphatic mono- and dicarboxylic acids such as acetic acid, propionic acid, succinic acid, formic acid, caprylic acid, maleic acid, oxalic acid, malonic acid, etc.; phenyl-substituted alkanoic acids, hydroxy alkanoic acid, aromatic carboxylic acids, and aliphatic and aromatic sulfonic acids such as methylbenzoic acid, phthalic acid, benzenesulfonic acid, phenylpropionate, tartaric acid, citric acid, lactic acid, glycollic acid, phenylacetic acid, phenylbutyric acid, methanesulfonic acid, etc.

Suitable amidinoureas for use in the veterinary treatment method of this invention are those disclosed in the Arzneimittel Forschung monograph identified above and in U.S. Pat. Nos. 4,115,647; 4,088,785; 4,025,652; 4,115,564; 4,060,635; and 4,058,557 and in co-pending application Ser. No. 671,762, the disclosures of which are incorporated herein by reference.

The amidinoureas employed as the principal active ingredient in the composition and method are prepared by methods known in the art.

Exemplary compounds prepared in accordance with such teachings for utilization in this invention are named below wherein the urea nitrogens are designated as positions 1 and 3 respectively:

1-(2,6-dimethylphenyl)-3-methylamidinourea
0-chlorophenylamidinourea
(2,3-dichlorophenylamidino)urea
(2,4-dichlorophenylamidino)urea
(2,5-dichlorophenylamidino)urea
(3,4-dichlorophenylamidino)urea
(3,5-dichlorophenylamidino)urea
(2,6-dichlorophenylamidino)urea
m-chlorophenylamidinourea
p-chlorophenylamidinourea
3,4-diflourophenylamidinourea
m-bromophenylamidinourea
p-bromophenylamidinourea
3,4-dibromophenylamidinourea
3-chloro-4-bromophenylamidinourea
3-bromo-4-chlorophenylamidinourea
3-chloro-4-fluorophenylamidinourea
3-bromo-4-fluorophenylamidinourea
3-fluoro-4-chlorophenylamidinourea
2,6-dimethylphenylamidinourea
2,6-diethylphenylamidinourea
2-methyl-6-ethylphenylamidinourea
2-methyl-6-methoxyphenylamidinourea
2-methyl-6-ethoxyphenylamidinourea
2-ethyl-6-ethoxyphenylamidinourea
3,4-dimethoxyphenylamidinourea
3,4-dihydroxyphenylamidinourea
3,4,5-trimethoxyphenylamidinourea
3,4,5-trihydroxyphenylamidinourea
1-(2,6-dimethylphenylamidino-3,3-(N-methyl-3'-azapentamethylene (urea)
1(2,6-dimethylphenylamidino)-3,3-(N-methyl-3'-azahexamethylene (urea)
1-(2,6-dimethylphenylamidino)-3,3-(3'-oxapentamethylene)urea
1-(2,6-dimethylphenylamidino)-3,3-(2'-thiatetramethylene)urea
1-(2,6-dimethylphenylamidino)-3,3-tetramethyleneurea
1-(p-fluorophenylamidino)-3,3-(a,a'-dimethylpentamethylene)urea
1-(p-chlorophenylamidino)-3,3-(pentamethylene)urea
1-(2,6- dimethylphenylamidino)-3,3-(αα'-dimethylpentamethylene)urea
1-(2,6-dimethylphenylamidino)-3,3-pentamethyleneurea
1-(2,6-dimethylphenylamidino)-3,3-(y-methylpentamethylene)urea
1-(N-methylamidino)-3-(2,6-dimethylphenyl)urea
1-(N-methylamidino)-3-(2,6-diethylphenyl)urea
1-amidino-3-(2-methyl-6-chlorophenyl)urea
1-amidino-3-(2-methyl-6-bromophenyl)urea
1-amidino-3-(2-methyl-6-methoxyphenyl)urea
1-amidino-3-(2,6-dimethylphenyl)urea
1-amidino-3-(2-methyl-6-ethylphenyl)urea
1-amidino-3-(2-ethyl-6-chlorophenyl)urea 1-amidino-3-(2-ethyl-6-bromophenyl)urea
1-amidino-3-(2,6-diethylphenyl)urea
1-amidino-3-methyl-3-(2-methyl-6-chlorophenyl)urea
1-amidino-3-methyl-3-(2-methyl-6-bromophenyl)urea
1-amidino-3-methyl-3-(2-methyl-6-methoxyphenyl)urea
1-amidino-3-methyl-3-(2,6-dimethylphenyl)urea
1-amidino-3-methyl-3-(2-methyl-6-ethylphenyl)urea
1-amidino-3-methyl-3-(2-ethyl-6-chlorophenyl)urea
1-amidino-3-methyl-3-(2-ethyl-6-bromophenyl)urea
1-amidino-3-methyl-3-(2-ethyl-6-methoxyphenyl)urea
1-amidino-3-methyl-3-(2,6-diethylphenyl)urea
1-amidino-3-(2-methyl-6-chlorophenyl)urea
1-amidino-3-(2-methyl-6-bromophenyl)urea
1-amidino-3-(2-methyl-6-methylphenyl)urea
1-amidino-3-(2,6-dimethylphenyl)urea
1-amidino-3-(2-methyl-6-ethylphenyl)urea
1-amidino-3-(2-ethyl-6-chlorophenyl)urea
1-amidino-3-(2-ethyl-6-bromophenyl)urea
1-amidino-3-(2-ethyl-6-methoxyphenyl)urea
1-amidino-3-(2,6-diethylphenyl)urea
1-amidino-3-methyl-3-(2-methyl-6-chlorophenyl)urea
1-amidino-3-methyl-3-(2-methyl-6-bromophenyl)urea
1-amidino-3-methyl-3-(2-methyl-6-methoxyphenyl)urea
1-amidino-3-methyl-3-(2,6-dimethylphenyl)urea
1-amidino-3-methyl-3-(2-methyl-6-ethylphenyl)urea
1-amidino-3-methyl-3-(2-ethyl-6-chlorophenyl)urea
1-amidino-3-methyl-3-(2-ethyl-6-bromophenyl)urea
1-amidino-3-methyl-3-(2-ethyl-6-methoxyphenyl)urea
1-amidino-3-methyl-3-(2,6-diethylphenyl)urea The amidinoureas of Formula I and their pharmaceutically acceptable salts are useful as veterinary medicines. In particular, these compounds are useful in preventing or treating scours in food-producing animals. The compounds are useful in the treatment of neonatal diarrhea in animals, particularly lambs, calves, and baby pigs. Scours in calves, lambs, baby pigs and foals can be prevented or improved by administering an effective amount of a compound of Formula I, preferably as a food additive, though other forms of administration can be used. As a food additive, the active amidinourea can be dispersed or dissolved in the normal diet or formulated as part of the animal feed or dissolved in the drinking water.

The compounds of Formula I, and especially those of Formula II and the specific compounds identified above, when formulated into therapeutic dosage forms, provide a beneficial means for the treatment of animal scours. The activity and recommended dosage amounts are shown by the following tests.

SWINE SCOURS STUDY

Doses of 1-(2,6-dimethylphenyl)-3-methylamidinourea hydrochloride that are well tolerated in piglets were determined as follows:

9 piglets, 5 to 6 days old, were treated. Three piglets received 1 mg. each, three received 5 mgs. each and three received 10 mgs. each. Each dose was dissolved in 1.1 ml. dH$_2$O and administered orally with a plunger applicator bottle to which was attached 6 cm. of polyethylene tubing. No clinical adverse effects were noted during the two-hour post-treatment observation period.

On the following day, the procedure was repeated on the same nine piglets using 30, 100 and 300 mg./each/3 pigs. Because of solubility difficulties each dose was administered in 2.2 ml. dH$_2$O. No adverse effects were noted in the three pigs receiving 30 mg. Their weights were 3.5, 4.0 and 5.25 lbs.

The results at 100 mg./pig, administered at 10:30 a.m. were as follows:
1.75 lbs.: convulsions, vomiting, died 1:20 p.m.
2.50 lbs: slight convulsions, convulsions, vomiting, died 1:00 p.m.
4.50 lbs: vomited at 11:20 p.m.

The results at 300 mg./pig, administered at 10:30 a.m. were as follows:
2.25 lbs: convulsions, died 11:15 a.m.
5.25 lbs: vomited at 11:40 a.m.
5.50 lbs: vomited at 1:15 p.m.

The three pigs that died were "posted" to determine cause of death. While the two that vomited had inhaled some of the material, death was caused by the drug.

FOLLOW-UP

Seven days later, a 30 mg. piglet died. Autopsy revealed thoracic cavity reddish and lungs consolidated. Ascites and periotonitis was evident in the abdominal cavity. Intestines were adhered to each other and the abdominal wall.

Eleven days later a 300 mg. piglet died. By necropsy on the twelfth day, the body was badly decomposed and examination revealed little. Both intestines were void of food and distended with gas. Twenty-three days later, the remaining piglets appeared to be normal. They were sacrificed on that day.

The efficacy of 1-(2,6-dimethylphenyl)-3-methylamidinourea hydrochloride was determined in naturally occuring "baby pig scours", alone and in combination with Neomycin, as follows:

A. Pre-Treatment

Litters of newborn pigs were selected at random for treatment. They were kept in the farrowing house under good management conditions but with no scours prophylaxis. Drug administrator and evaluator were blinded.

B. Treatment

Time of birth was recorded. When the first piglet in each litter was positively identified for scours, it was treated with one dose of one of six regimens:
1. 1.0 mg. 1-(2,6-dimethylphenyl)-3-methylamidinourea hydrochloride
2. 1.0 mg. 1-(2,6-dimethylphenyl)-3-methylamidinourea hydrochloride plus 50 mg. neomycin sulfate
3. 10.0 mg. 1-(2,6-dimethylphenyl)-3-methylamidinourea hydrochloride
4. 10.0 mg. 1-(2,6-dimethylphenyl)-3-methylamidinourea hydrochloride
5. 50 mg. neomycin sulfate
6. Distilled water Each dose was dissolved in 1.1 ml. dH$_2$O and administered orally with a plunger applicator bottle to which was attached 6 cm. of polyethylene tubing.

As littermates of the affected piglet scoured, they were also treated. At approximately six hours after the first piglet scoured, all untreated (non-scouring) piglets were treated.

C. Post-Treatment

All litters were observed intensively for four days after treatment and periodically for the next seven days. All observations were recorded and are summarized on the following charts.

Pen No. 24
Treatment: 1-(2,6-dimethylphenyl)-3-methylamidinourea hydrochloride (1 mg)
Birthdate: April 22

| PIGLET | SCOURS | TIME | COMMENTS |
| --- | --- | --- | --- |
| 1 | Y | 1200 | |
| 2 | Y | 1215 | |
| 3 | Y | 1345 | |
| 4 | N | 1730 | 4/26, died, some food in stomach and intestine |
| 5 | N | | |
| 6 | N | | |
| 7 | Y | | |
| 8 | N | | |
| 9 | N | | 4/26, died, no food in GI tract, upper intestine pale, lower congested. |
| 10 | Y | | |
| 11 | N | | |
| | | | 4/22, severe diarrhea |
| 12 | N | | 4/27, died, stomach distended with gas, no food, upper intestine pale, lower congested. |
| 13 | N | | |
| 14 | N | | |

Other Observations:
4/24, one dead, no autopsy
4/28, two weak
4/29, above piglets eating
Summary: 5 scoured, 4 or 5 survived.
Pen No. 34
Treatment: 1 mg. 1-(2,6-dimethylphenyl-3-methylamidinourea hydrochloride plus 50 mg. neomycin sulfate
Birthdate: 4/12

| PIGLET | SCOURS | TIME | COMMENTS |
| --- | --- | --- | --- |
| 1 | Y | 1115 | |
| 2 | Y | 1115 | |
| 3 | Y | 1345 | |
| 4 | N | 1615 | |
| 5 | N | | |
| 6 | N | | all piglets normal |
| 7 | N | | |
| 8 | ? | | |
| 9 | N | | |
| 10 | N | | |
| 11 | N | | |
| 12 | N | | |

SUMMARY: 3 scoured, all survived.
Pen No. 36
Treatment: 10 mg. 1-(2,6-dimethylphenyl)-3-methylamidinourea hydrochloride
Birthdate: 4/13

| PIGLET | SCOURS | TIME | COMMENTS |
| --- | --- | --- | --- |
| 1 | Y | 830 | |
| 2 | Y | 855 | scoured again at 1800 |
| 3 | Y | 855 | diarrhea stopped by 1000, scoured again at 1800 |
| 4 | Y | 855 | diarrhea stopped by 1000 |
| 5 | Y | 855 | diarrhea stopped by 1000, scoured again at 1800 |
| 6 | Y | 935 | diarrhea stopped by 1000 |
| 7 | N | 1300 | |
| 8 | N | 1300 | |

Other observations: 4/15 no scours, some bloating. Severe, propulsive scours before treatment.
Summary: 6 scoured, all survived.
Pen No. 35
Treatment: 10 mg. 1-(2,6-dimethylphenyl)-3-methylamidinourea hydrochloride plus 50 neomycin sulfate
Birthdate: 4/12

| PIGLET | SCOURS | TIME | COMMENTS |
| --- | --- | --- | --- |
| 1 | Y | 1120 | |
| 2 | Y | 1125 | |
| 3 | Y | 1125 | 4/15 dead, abdomen distended stomach and intestine full of gas. Stomach filled with milk, intestine with soft fecal material. Remaining animals bloated, signs of constipation |
| 4 | Y | 1305 | |
| 5 | Y | 1305 | |
| 6 | Y | 1310 | |
| 7 | Y | 1315 | |
| 8 | N | 1625 | |
| 9 | N | 1625 | |
| 10 | N | 1625 | |
| 11 | N | 1625 | |

Other Observations:
4/14, all piglets apparently normal
4/16, still bloating, but nursing normally
4/17, piglets normal
Summary: 7 scoured, 6 survived.
Pen No. 30
Treatment: 50 mg. neomycin sulfate
Birthdate: 4/12

| PIGLET | SCOURS | TIME | COMMENTS |
| --- | --- | --- | --- |
| 1 | Y | 1100 | |
| 2 | Y | 1100 | 4/18, dead, dehydrated, no autoposy- "runt" |
| 3 | Y | 100 | |
| 4 | Y | 1100 | |
| 5 | Y | 1105 | |
| 6 | Y | 1245 | 4/14, scours seen again, 945 |
| 7 | Y | 1245 | |
| 8 | Y | 1250 | |
| 9 | N | 1610 | 4/15, died, probably crushed by sow. No food in stomach. GI tract distended with gas, small amount of soft material throughout intestines. Evidence of soft feces around anus and tail. |
| 10 | N | 1610 | |
| 11 | N | 1610 | |
| 12 | N | 1610 | |
| 13 | N | 1610 | |

Other Observations: 4/19, all piglets normal
Summary: 8 scoured, 7 survived.
Pen No. 1
Treatment: Distilled Water
Birthdate: 4/21

| PIGLET | SCOURS | TIME | COMMENT |
| --- | --- | --- | --- |
| 1 | Y | 1140 | |
| 2 | Y | 1145 | |
| 3 | Y | 1215 | |
| 4 | Y | 1330 | |
| 5 | Y | 1515 | |
| 6 | Y | 1515 | |
| 7 | Y | 1520 | |
| 8 | Y | 1600 | |
| 9 | N | 1730 | |
| 10 | N | 1730 | 4/25, dead |

| PIGLET | SCOURS | TIME | COMMENT |
|---|---|---|---|
| 11 | N | 1730 | autopsy - upper part of intestine pale, lower part congested. |
| 12 | N | 1730 | |

Other Observations:
4/27, one dead, number illegible, autopsy unremarkable
4/28, two very weak, numbers illegible, one unable to stand
4/29, one dead, number illegible, dehydrated, autopsy—stomach and intestines distended with gas, no food in stomach, small amount hard feces in large intestine.
Summary: 8 scoured, probably 5 survived.

SUMMARY

These results from six litters (70 piglets) demonstrate that 1-(2,6-dimethylphenyl)-3-methylamidinourea hydrochloride is at least as effective as neomycin in stopping scours, though it can also be used in combination with neomycin or other medication as an effective treatment or preventive for scours in calves, lambs and piglets, particularly when less than 10 days old.

The compositions of the present invention can be prepared in forms suitable for administration by compounding an effective single dose amount of a compound of Formula I above with known ingredients generally employed in the preparation of therapeutic veterinary compositions provided as tablets, capsules, lozenges, chewable lozenges, pills, powder, granules, suspensions, oil-in-water or water-in-oil emulsions, or other similar forms which can be taken orally. Or, the treatment can be accomplished by incorporating an effective amount of a compound of Formula I in the animal diet as a feed supplement or dissolved in the animal's fluid intake.

Since the compounds are readily absorbed into the bloodstream from the stomach and intestines when taken orally, the preferred method of treatment is to give the drug orally which is also the safest and most practical route of administration. Optional methods can be used. Where, for example, the animal is not eating or cannot swallow or has difficulty in swallowing, other methods of administration which permit the drug to be absorbed from the gastrointestinal tract or which deliver a solution of the drug directly to the bloodstream can be employed.

The dosage regimens in carrying out the anti-scouring methods utilizing the amidinourea compositions of this invention are those which insure maximum therapeutic response until improvement is obtained and thereafter the minimum effective level which gives relief. Thus, in general, the dosages are those that are therapeutically effective in the treatment of scours. For calves, lambs, piglets and foals, the average effective dose is between about 2 and about 10 mg./kg. of body weight, while for adult cattle, a slightly lower total dose is recommended.

In general, the single oral dose for piglets weighing between about 1 and 5 lbs. will contain between about 1 mg. and 25 mg. (preferably in the range of 5 to 15 mg.). Similar doses of about 1 to 50 mg. are employed for lambs of about 5 to 20 lbs. and doses of 5 to 75 mg., preferably 20 to 50 mg. for calves of about 10 to 50 lbs. Fractional or multiple doses can of course be given bearing in mind that in selecting the appropriate dosage in any specific case, consideration must be given to weight, general health, age, and other factors which may influence response to the drug. The drug response on oral administration usually follows within 10 to 30 minutes after administration and is maintained for 1 to 4 hours. The drug is generally given in single doses 2 to 4 times daily or as required to maintain an effective drug level in the blood stream for continuous relief of scours.

Compositions intended for oral use may be prepared according to methods known generally in the art, such compositions may contain one or more agents selected from the group consisting of sweetening agents, flavoring agents, coloring agents, and preserving agents, in order to provide a pharmaceutically elegant and palatable preparation. Orally, they may be administered in tablets, lozenges, aqueous or oily suspensions, dispersible powders or granules, emulsions, hard or soft capsules, or syrups or elixers which contain the active amidinourea ingredient in admixture with non-toxic pharmaceutically acceptable excipients. Excipients which may be, for example, inert diluents, such as calcium carbonate, sodium carbonate, lactose, calcium phosphate or sodium phosphate; granulating and disintegrating agents, for example, maize starch or alginic acid; binding agents, for example, starch, gelatin or acacia; and lubricating agents, for example, magnesium stearate, stearic acid or talc. The tablets may be uncoated or they may be coated by known techniques to make them more effective for example to delay disintegration or absorption or to make them more palatable or for other reasons for which orally-administered drugs have been previously provided in coated form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with an oil medium, for example, arachis oil, liquid paraffin or olive oil.

Aqueous solutions containing the active amidinourea form a further embodiment of this invention. Excipients suitable for aqueous suspensions, may be employed, if desired. These excipients are suspending agents, for example, sodium carboxymethyl-cellulose, methyl-cellulose, hydroxypropyl-methylcellulose, sodium alginate, polyvinylpyrrolidine, gum tragacanth and gum acacia; dispersing or wetting agents may be a naturally occurring phosphatide, for example, lecithin; or condensation products or an alkylene oxide with fatty acids, for example, polyoxyethylene stearate; or condensation products of ethylene oxide with long-chain aliphatic alcohols, for example, heptadecaethylenoexycetanol; or condensation products of ethylene oxide with partial esters derived from fatty acids and a hexitol, for example, polyoxyethylene sorbitol mono-oleate; or condensation products of ethylene oxide with partial esters derived from fatty acids and hexitol anhydrides, for example, polyoxyethylene sorbitan monoleate. The said aqueous suspensions may also contain one or more preservatives, for example, ethyl, or n-propyl, p-hydroxy benzoate, one or more coloring agents, one or more flavoring agents, and one or more sweetening agents, such as sucrose.

Oily suspensions may be formulated by suspending the active ingredient in a vegetable oil, for example, arachis oil, olive oil, sesame oil, or coconut oil, or in a mineral oil such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending or wetting agents and suspending agents are exemplified by those already mentioned above. Additional excipients, for example, sweetening, flavoring and coloring agents, may also be present.

The compounds of this invention may also be in the form of oil-in-water emulsions. The oily phase may be a vegatable oil, for example, olive oil or arachis oils, or a mineral oil, for example, liquid paraffin or mixtures of these. Suitable emulsifying agents may be naturally-occurring gums, for example, gum acacia or gum tragacanth, naturally-occurring phosphatides, for example, soya bean lecithin, and esters or partial esters derived from fatty acids and hexitol anhydrides, for example, sorbitan mono-oleate. The emulsions may also contain sweetening and flavoring agents.

Syrups and elixers may be formulated with sweetening agents, for example, glycerol, sorbitol or sucrose. Such formulations may also contain a demulcent, a preservative and flavoring and coloring agents. The pharmaceutical compositions may be in the form of a sterile injectionable preparation, for example, as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example, as an aqueous solution buffered to a pH of 4.0 to 7.0 and made isotonic with sodium chloride.

Further, the active amidinourea may be administered alone or in admixture with other agents having the same or different pharmacological properties.

The anti-scour treatment can be administered in combination with antibiotics such as neomycin or with other antibacterial or antiviral agents, or other adjuvants such as electrolytes and antiemetics. The compounds of Formula I can also be used as a preventive measure, in which case, the preferred mode of administration is through the diet as a feed or water additive.

For the treatment of scours, the compounds of Formula I, and particularly the compounds of Formula II, and the specifically named compounds noted above, are administered orally to the infant animals for example with a plunger applicator bottle at doses in the order of 0.5 to 25 mg./kg of body weight, preferably about 5 to 15 mg/kg administered 1 to 4 times daily. Higher doses can be used when tolerated especially in the case of larger animals. In general, a dose of about 10 mg. per day is effective in relieving symptoms of scours in calves, piglets, lambs and foals. The treatments are preferably administered prophylactically or within about 10 hours (preferably within about 5 hours) after onset of scours. The treatments have been found to be especially effective in scouring animals less than ten days old.

The veterinary compositions and method of this invention are further illustrated by the following examples of therapeutic compositions incorporating an effective amidinourea in forms suitable for administration to diseased animals.

EXAMPLE 1

Therapeutic compositions of the invention are prepared by using known techniques for compounding employing either the base or a salt as the active ingredient along with the non-toxic excipients chosen in accordance with the particular form and properties desired for the therapeutic composition.

Tablets which can be advantageously used for either remedial or prophylactic treatments can be provided in a form which provides relief when administered at a rate of 2 to 4 tablets per day containing between about 5 and 25 mg. of the active ingredient. An exemplary formulation which can be utilized is, for example, the following:

| | |
|---|---|
| 1-(2,6-dimethylphenyl)-3-methylamidinourea hydrochloride | 500 mg. |
| tricalcium phosphate | 200 mg. |
| talc | 50 mg. |
| magnesium stearate | 10 mg. |
| polyvinyl acetate | 40 mg. |

In addition, there are added protective excipients such as ethylcellulose, dibutylphthalate, propylene glycol, wax (white and/or carbauba), spermaceti, methylene chloride, and rectified diethyl ether. The ingredients are compressed to minimum size to provide a tablet of about 850 mg.

EXAMPLE 2

A lot of tablets each containing 20 mg. of 1-(2,6-dimethylphenyl)-3-methylamidinourea hydrochloride is prepared from the following types and amounts of ingredients:

| | |
|---|---|
| 1-(2,6-dimethylphenyl)-3-methylamidinourea hydrochloride | 1 kg. |
| dicalcium phosphate | 1 kg. |
| methylcellulose USP | 75 g. |
| talc | 150 g. |
| cornstarch | 200 g. |
| magnesium stearate | 10 g. |

The active ingredient and dicalcium phosphate are mixed thoroughly and granulated with a 7.5% solution of methylcellulose in water and passed through a #8 screen and air-dried. The dried granules are passed through a #12 screen and combined with the talc, starch and magnesium stearate with thorough mixing after which the composition is compressed into tablets.

EXAMPLE 3

A lot of 2-piece hard gelatin capsules, each containing 25 mg. of 1-(2,6-dimethylphenyl)-3-methylamdinourea hydrochloride are prepared from the following types and amounts of ingredients:

| | |
|---|---|
| 1-(2,6-dimethylphenyl)-3-methylamidinourea hydrochloride | 500 g. |
| dicalcium phosphate | 500 g. |
| talc | 150 g. |
| magnesium stearate | 5 g. |

The ingredients are mixed thoroughly and filled into capsules which are used for oral administration at the rate of about one every four hours. If desired, slow release forms can be provided or delay release forms depending on choice of capsules and formulating ingredients.

EXAMPLE 4

A sterile solution suitable for interperitoneal injection, and containing 10 mg. of 1-(2,6-dimethylphenyl)-3-methylamidinourea hydrochloride in each, 10 ml. (1:1 wt./volume), is prepared from the following ingredients:

| | |
|---|---|
| 1-(2,6-dimethylphenyl)-3-methylamidinourea hydrochloride | 10 g. |
| benzyl benzoate | 100 ml. |
| methylparaben | 1 g. |
| propylparaben | 0.5 g. |
| cottonseed oil q.s. | 500 ml. |

EXAMPLE 5

Tablets for oral use, each containing 25 mg. of 1-(2,6-dimethylphenyl)-3-methylamidinourea hydrochloride are prepared from the following types and amounts of material:

| | |
|---|---|
| 1-(2,6-dimethylphenyl)-3-methylamidinourea hydrochloride | 500 g. |
| lactose U.S.P. | 350 g. |
| potato starch U.S.P. | 346 g. |

The mixture is moistened with an alcoholic solution of 20 g. of stearic acid and granulated through a sieve. After drying, the following ingredients are added:

| | |
|---|---|
| potato starch U.S.P. | 320 g. |
| talc | 400 g. |
| magnesium stearate | 500 g. |
| colloidal silicium dioxide | 64 g. |

The mixture is thoroughly mixed and compressed into tablets.

EXAMPLE 6

Five hundred ampoules each with 2 ml. of solution which contains 15 mg. of 1-(2,6-dimethylphenyl)-3-methylamidinourea hydrochloride are prepared from the following types and amounts of materials:

| | |
|---|---|
| 1-(2,6-dimethylphenyl)-3-methylamidinourea hydrochloride | 7.5 g. |
| ascorbic acid | 1 g. |
| sodium bisulphite | 0.5 g. |
| sodium sulphite | 1 g. |

EXAMPLE 7

Capsules are prepared as follows:

15 g. of 1-(2,6-dimethylphenyl)-3-methylamidinourea hydrochloride, 3 g. magnesium stearate, 2 g. of finely divided silica sold under the trademark CAB-O-SIL by Godfrey L. Cabot, Inc., Boston, Mass., and, 369 g. of lactose.

The ingredients are mixed with each other and the mixture is filled in gelatin capsules. Each capsule contains 500 mg. of the composition and thus, 15 mg. of 1-(2,6-dimethylphenyl)-3-methylamidinourea hydrochloride.

EXAMPLE 8

50 g. of 1-(2,6-dimethylphenyl)-3-methylamidinourea hydrochloride, 5 g. of propyl p-hydroxybenzoate are dissolved and dilluted to 5000 cc. with twice distilled water after the addition of modified Sorensen buffer solution in an amount sufficient to adjust the pH value to a pH of 6.0. Sodium chloride is dissolved therein in an amount sufficient to render the resulting solution isotonic. The final solution is passed through a bacteriological filter and the filtrate is autoclaved at 120° C. for 15 minutes to yield a parenterally applicable solution which contains 50 mg. of 1-(2,6-dimethylphenyl)-3-methylamidinourea hydrochloride in 5 cc.

By analogous procedures, other amidinoureas can be prepared from the corresponding starting materials and formulated for either oral administration as injectible or infusible solutions or for rectal administration, for example, suppository form. The solid and liquid formulations can be dispersed in the feed or dissolved in drinking water or the liquid diet.

We claim:

1. A method of treating scours in calves, lambs, piglets or foals which comprises administering to the afflicted animal an effective amount of an anti-scouring agent of the formula:

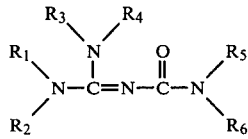

wherein one of $R_1$ and $R_5$ is phenyl, phenyl in which one or more of the hydrogens is substituted by halo, lower alkyl, halo lower alkyl, nitro, lower alkoxy, hydroxy, aryl lower alkoxy, acyloxy, cyano, halo lower alkoxy, or lower alkyl sulfonyl; aralkyl, pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and the other of $R_1$ and $R_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alklyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when $R_1$ is phenyl, phenyl substituted as above, aralkyl, pyridyl or pyridyl substituted as above, $R_5$ together with $R_6$ and the nitrogen to which $R_5$ and $R_6$ are attached may form a 5 or 6 membered heterocyclic ring which may include 0 to 2 additional hetero atoms which may be either oxygen, nitrogen or sulfur; and when R$_5$ is phenyl, phenyl substituted as above, R$_1$ and R$_2$ together with the nitrogen to which they are attached may be a 5 or 6 membered heterocyclic ring which may include 0 to 2 additional hetero atoms which may be either oxygen, nitrogen or sulfur; and R$_3$ and R$_4$ are each independently hydrogen, lower alkyl, lower alkoxy, lower alkenyl, lower alkynyl, cyclo lower alkyl or aralkyl; and their pharmaceutically acceptable acid addition salts.

2. A method according to claim 1 wherein the anti-scouring agent is a compound of the formula:

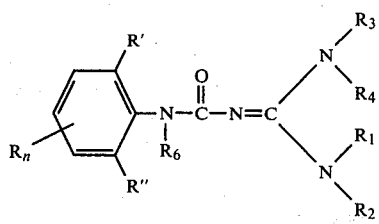

wherein R$_1$, R$_2$, R$_3$, R$_4$ and R$_5$ are each independently hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and R$_n$ represents one, two or three substituents in any one or more of the para and meta positions which substituents may be hydrogen, halo, lower alkyl, halo lower alkyl, nitro, lower alkoxy, hydroxy, aryl lower alkoxy, acyloxy, halo lower alkoxy, or lower alkyl sulfonyl; R' and R" are hydrogen, halo, lower alkyl, halo lower alkyl, nitro, lower alkoxy, hydroxy, aryl lower alkoxy, acyloxy, halo lower alkoxy, or lower alkyl sulfonyl; and their pharmaceutically acceptable acid addition salts.

3. A method according to claim 2 wherein the anti-scouring agent is a compound of the formula:

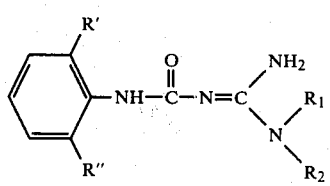

wherein R$_1$ and R$_2$ are each hydrogen, lower alkyl, lower alkoxy or hydroxy; and R' and R" are each hydrogen, halo, or lower alkyl; and their pharmaceutically acceptable acid addition salts.

4. A method of treating scours in calves which comprises administering to the afflicted animal 0.5 to 25 mg/kg, 1 to 4 times daily of an anti-scouring agent of the formula:

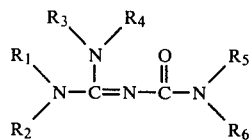

wherein one of R$_1$ and R$_5$ is phenyl, phenyl in which one or more of the hydrogens is substituted by halo, lower alkyl, halo lower alkyl, nitro, lower alkoxy, hydroxy, aryl lower alkoxy, acyloxy, cyano, halo lower alkoxy, or lower alkyl sulfonyl; aralkyl, pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and the other of R$_1$ and R$_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; R$_2$ and R$_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when R$_1$ is phenyl, phenyl substituted as above, aralkyl, pyridyl, or pyridyl substituted as above, R$_5$ together with R$_6$ and the nitrogen to which R$_5$ and R$_6$ are attached may form a 5 or 6 membered heterocyclic ring which may include 0 to 2 additional hetero atoms which may be either oxygen, nitrogen or sulfur; and when R$_5$ is phenyl, phenyl substituted as above, R$_1$ and R$_2$ together with the nitrogen to which they are attached may be a 5 or 6 membered heterocyclic ring which may include 0 to 2 additional hetero atoms which may be either oxygen, nitrogen or sulfur; and R$_3$ and R$_4$ are each independently hydrogen, lower alkyl, lower alkoxy, lower alkenyl, lower alkynyl, cyclo lower alkyl or aralkyl; and their pharmaceutically acceptable acid addition salts.

5. A method according to claim 4 wherein the treated calves are less than 10 days old.

6. A method according to claim 4 wherein the anti-scouring agent is 1-(2,6-dimethylphenyl)-3-methylamidinourea.

7. A method according to claim 4 wherein the anti-scouring agent is 1-(2,6-dimethylphenyl)-3-methylamidinourea hydrochloride.

8. A method of treating scours in piglets which comprises administering to the afflicted animal 0.5 to 25 mg/kg, 1 to 4 times daily of an anti-scouring agent of the formula:

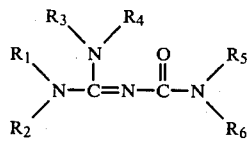

wherein one of $R_1$ and $R_5$ is phenyl, phenyl in which one or more of the hydrogens is substituted by halo, lower alkyl, halo lower alkyl, nitro, lower alkoxy, hydroxy, aryl lower alkoxy, acyloxy, cyano, halo lower alkoxy, or lower alkyl sulfonyl; aralkyl, pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and the other of $R_1$ and $R_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when $R_1$ is phenyl, phenyl substituted as above, aralkyl, pyridyl, or pyridyl substituted as above, $R_5$ together with $R_6$ and the nitrogen to which $R_5$ and $R_6$ are attached may form a 5 or 6 membered heterocyclic ring which may include 0 to 2 additional hetero atoms which may be either oxygen, nitrogen or sulfur; and when $R_5$ is phenyl, phenyl substituted as above, $R_1$ and $R_2$ together with the nitrogen to which they are attached may be a 5 or 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl; and their pharmaceutically acceptable acid addition salts.

9. A method according to claim 8 wherein the treated piglets are less than 10 days old.

10. A method according to claim 8 wherein the anti-scouring agent is 1-(2,6-dimethylphenyl)-3-methylamidinourea.

11. A method according to claim 8 wherein the anti-scouring agent is 1-(2,6-dimethylphenyl)-3-methylamidinourea hydrochloride.

12. A method of treating scours in lambs which comprises administering to the afflicted animal 0.5 to 25 mg/kg, 1 to 4 times daily of an anti-scouring agent of the formula:

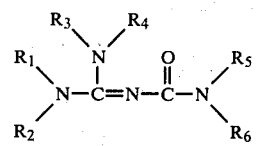

wherein one of $R_1$ and $R_5$ is phenyl, phenyl in which one or more of the hydrogens is substituted by halo, lower alkyl, halo lower alkyl, nitro, lower alkoxy, hydroxy, aryl lower alkoxy, acyloxy, cyano, halo lower alkoxy, or lower alkyl sulfonyl; aralkyl, pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and the other of $R_1$ and $R_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when $R_1$ is phenyl, phenyl substituted as above, aralkyl, pyridyl, or pyridyl substituted as above, $R_5$ together with $R_6$ and the nitrogen to which $R_5$ and $R_6$ are attached may form a 5 or 6 membered heterocyclic ring which may include 0 to 2 additional hetero atoms which may be either oxygen, nitrogen or sulfur; and when $R_5$ is phenyl, phenyl substituted as above, $R_1$ and $R_2$ together with the nitrogen to which they are attached may be a 5 or 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl; and their pharmaceutically acceptable acid addition salts.

13. A method according to claim 12 wherein the treated lambs are less than 10 days old.

14. A method according to claim 12 wherein the anti-scouring agent is 1-(2,6-dimethylphenyl)-3-phenyl-amidinourea.

15. A method according to claim 12 wherein the anti-scouring agent is 1-(2,6-dimethylphenyl)-3-methyl-amidinourea hydrochloride.

16. A method of treating scours in foals which comprises administering to the afflicted animal 0.5 to 25 mg/kg, 1 to 4 times daily of an anti-scouring agent of the formula:

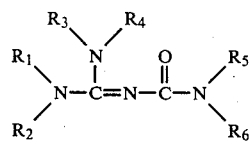

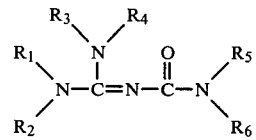

wherein one of $R_1$ and $R_5$ is phenyl, phenyl in which one or more of the hydrogens is substituted by halo, lower alkyl, halo lower alkyl, nitro, lower alkoxy, hydroxy, aryl lower alkoxy, acyloxy, cyano, halo lower alkoxy, or lower alkyl sulfonyl; aralkyl, pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and the other of $R_1$ and $R_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when $R_1$ is phenyl, phenyl substituted as above, aralkyl, pyridyl, or pyridyl substituted as above, $R_5$ together with $R_6$ and the nitrogen to which $R_5$ and $R_6$ are attached may form a 5 or 6 membered heterocyclic ring which may include 0 to 2 additional hetero atoms which may be either oxygen, nitrogen or sulfur; and when $R_5$ is phenyl, phenyl substituted as above, $R_1$ and $R_2$ together with the nitrogen to which they are attached may be a 5 or 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl; and their pharmaceutically acceptable acid addition salts.

17. A method according to claim 16 wherein the treated foals are less than 10 days old.

18. A method according to claim 16 wherein the anti-scouring agent is 1-(2,6-dimethylphenyl)-3-methylamidinourea.

19. A method according to claim 16 wherein the anti-scouring agent is 1-(2,6-dimethylphenyl)-3-methylamidinourea hydrochloride.

20. A method of treating winter bovine scours which comprises treating adult cattle with 0.5 to 25 mg/kg, 1 to 4 times daily of an anti-scouring agent of the formula:

wherein one of $R_1$ and $R_5$ is phenyl, phenyl in which one or more of the hydrogens is substituted by halo, lower alkyl, halo lower alkyl, nitro, lower alkoxy, hydroxy, aryl lower alkoxy, acyloxy, cyano, halo lower alkoxy, or lower alkyl sulfonyl; aralkyl, pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and the other of $R_1$ and $R_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alklyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when $R_1$ is phenyl, phenyl substituted as above, aralkyl, pyridyl or pyridyl substituted as above, $R_5$ together with $R_6$ and the nitrogen to which $R_5$ and $R_6$ are attached may form a 5 or 6 membered heterocyclic ring which may include 0 to 2 additional hetero atoms which may be either oxygen, nitrogen or sulfur; and when $R_5$ is phenyl, phenyl substituted as above, $R_1$ and $R_2$ together with the nitrogen to which they are attached may be a 5 or 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl; and their pharmaceutically acceptable acid addition salts.

21. A method according to claim 20 wherein the anti-scouring agent is a compound of the formula:

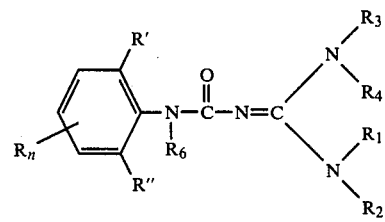

wherein $R_1$, $R_2$, $R_3$, $R_4$ and $R_6$ are each independently hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and $R_n$ represents one, two or three substituents in any one or more of the para and meta positions which substituents may be hydrogen, halo, lower alkyl, halo lower alkyl, nitro, lower alkoxy, hydroxy, aryl lower alkoxy, acyloxy, halo lower alkoxy, or lower alkyl sulfonyl; R' and R" are hydrogen, halo, lower alkyl, halo lower alkyl, nitro, lower alkoxy, hydroxy, aryl lower alkoxy, acyloxy, halo lower alkoxy, or lower alkyl sulfonyl; and their pharmaceutically acceptable acid addition salts.

22. A method according to claim 21 wherein the anti-scouring agent is a compound of the formula:

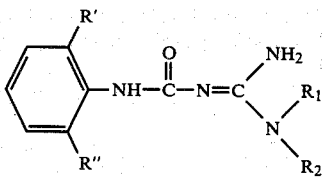

wherein $R_1$ and $R_2$ are each hydrogen, lower alkyl, lower alkoxy or hydroxy; and R' and R" are each hydrogen, halo, or lower alkyl; and their pharmaceutically acceptable acid addition salts.

23. A method of treating scours in calves, lambs, foals or piglets which comprises administering to the afflicted animal between 0.5 and 25 mg/kg, 1 to 4 times daily of an antiscouring agent of the formula:

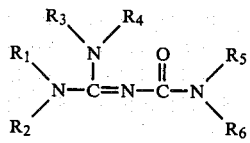

wherein one of $R_1$ and $R_5$ is phenyl, phenyl in which one or more of the hydrogens is substituted by halo, lower alkyl, halo lower alkyl, nitro, lower alkoxy, hydroxy, aryl lower alkoxy, acyloxy, cyano, halo lower alkoxy, or lower alkyl sulfonyl; aralkyl, pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and the other of $R_1$ and $R_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when $R_1$ is phenyl, phenyl substituted as above, aralkyl, pyridyl or pyridyl substituted as above, $R_5$ together with $R_6$ and the nitrogen to which $R_5$ and $R_6$ are attached may form a 5 or 6 membered heterocyclic ring which may include 0 to 2 additional hetero atoms which may be either oxygen, nitrogen or sulfur; and when $R_5$ is phenyl, phenyl substituted as above, aralkyl, pyridyl or pyridyl substituted as above, $R_1$ and $R_2$ together with the nitrogen to which they are attached may be a 5 or 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl; and their pharmaceutically acceptable acid addition salts.

24. A method of treating scours in calves, lambs, foals or piglets which comprises administering to the afflicted animal between 0.5 and 25 mg/kg, 1 to 4 times daily of an anti-scouring agent of the formula:

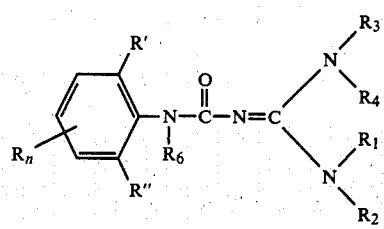

wherein $R_1$, $R_2$, $R_3$, $R_4$ and $R_6$ are each independently hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and $R_n$ represents one, two or three substituents in any one or more of the para and meta positions which substituents may be hydrogen, halo lower alkyl, halo lower alkyl, nitro, lower alkoxy, hydroxy, aryl lower alkoxy, acyloxy, halo lower alkoxy, or lower alkyl sulfonyl; R' and R" are hydrogen, halo, lower alkyl, halo lower alkyl, nitro, lower alkoxy, hydroxy, aryl lower alkoxy, acyloxy, halo lower alkoxy, or lower alkyl sulfonyl; and their pharmaceutically acceptable acid addition salts.

25. A method of treating scours in calves, lambs, foals or piglets which comprises administering to the afflicted animal between 0.5 to 25 mg/kg, 1 to 4 times daily, of an anti-scouring agent of the formula:

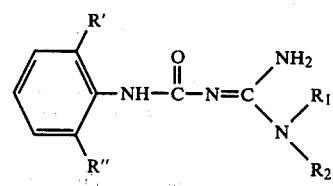

wherein $R_1$ and $R_2$ are each hydrogen, lower alkyl, lower alkoxy or hydroxy; and R' and R" are each hydrogen, halo, or lower alkyl; and their pharmaceutically acceptable acid addition salts.

26. A method of treating scours in calves, lambs, foals or piglets which comprises administering to the afflicted animal between 0.5 to 25 mg/kg, 1 to 4 times daily, of an antiscouring agent of the formula:

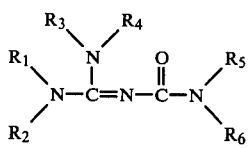

wherein one of $R_1$ and $R_5$ is aralkyl, pyridyl, or pyridyl having one or more of the hydrogens replaced by lower alkyl, lower alkoxy, halo, halo lower alkyl, amino, nitro, hydroxy, cyano, carboxyl or lower alkyl sulfonyl; and the other of $R_1$ and $R_5$ is hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono or di-lower alkyl, amino lower alkyl, carbamoyl lower alkyl, mono or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when $R_1$ is aralkyl, pyridyl or pyridyl substituted as above, $R_5$ together with $R_6$ and the nitrogen to which $R_5$ and $R_6$ are attached may form a 5 or 6 membered heterocyclic ring which may include 0 to 2 additional hetero atoms which may be either oxygen, nitrogen or sulfur; and when $R_5$ is aralkyl, pyridyl, or pyridyl substituted as above, $R_1$ and $R_2$ together with the nitrogen to which they are attached may be a 5 or 6 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl; and their pharmaceutically acceptable acid addition salts.

* * * * *

UNITED STATES PATENT AND TRADEMARK OFFICE
CERTIFICATE OF CORRECTION

PATENT NO. : 4,285,972
DATED : August 25, 1981
INVENTOR(S) : Billy J. Chou et al It is certified that error appears in the above—identified patent and that said Letters Patent is hereby corrected as shown below:

| | |
|---|---|
| Col. 9, 1st table | Comment beginning "4/26, died..." should appear opposite Piglet 8. |
| Col. 9, 1st table | Comment beginning "4/22, severe..." should appear opposite Piglet 11. |
| Col. 9, 1st table | Comment beginning "4/27, died..." should appear opposite Piglet 12. |
| Col. 10, 1st table | Comment beginning "4/15 dead..." should appear opposite Piglet 4. |
| Col. 10, 2nd table | "3 Y 100" should read --3 Y 1100--. |
| Col. 10, 3rd table | Comment "4/25, dead" should appear opposite Piglet 11 in column 11. |
| Col. 17, line 26 | "$R_5$" should read --$R_6$--. |

Signed and Sealed this

Twenty-second Day of June 1982

[SEAL]

Attest:

Attesting Officer

GERALD J. MOSSINGHOFF
Commissioner of Patents and Trademarks